(12) United States Patent
Lynch et al.

(10) Patent No.: US 8,618,112 B2
(45) Date of Patent: Dec. 31, 2013

(54) CRYSTALLINE FORMS OF AN INHIBITOR OF 11-β-HYDROXYSTEROID DEHYDROGENASE TYPE 1

(75) Inventors: Joseph E. Lynch, Plainfield, NJ (US); Yuri Y. Bereznitski, South River, NJ (US); Frederick T. Mattrey, Bridgewater, NJ (US); John L. Leazer, Jr., Metuchen, NJ (US); Russell R. Ferlita, Tampa, FL (US); Jinchu Liu, Edison, NJ (US); Jungjun Yin, Green Brook, NJ (US); Robert M. Wenslow, Jr., Cream Ridge, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 168 days.

(21) Appl. No.: 13/133,516

(22) PCT Filed: Dec. 7, 2009

(86) PCT No.: PCT/US2009/066939
§ 371 (c)(1),
(2), (4) Date: Jun. 8, 2011

(87) PCT Pub. No.: WO2010/068580
PCT Pub. Date: Jun. 17, 2010

(65) Prior Publication Data
US 2011/0237634 A1    Sep. 29, 2011

Related U.S. Application Data

(60) Provisional application No. 61/121,994, filed on Dec. 12, 2008.

(51) Int. Cl.
A61K 31/41   (2006.01)
A61K 31/4196  (2006.01)
C07D 249/08  (2006.01)
C07D 401/04  (2006.01)

(52) U.S. Cl.
USPC ........... 514/256; 514/331; 514/340; 514/364; 544/333; 548/131; 548/167; 548/203; 548/266.2

(58) Field of Classification Search
USPC .................. 514/256, 311, 340, 364; 544/333; 548/131, 167, 203, 266.2
See application file for complete search history.

(56) References Cited

U.S. PATENT DOCUMENTS

| | | | |
|---|---|---|---|
| 3,263,484 A * | 8/1966 | Watson et al. | 374/11 |
| 6,849,636 B2 * | 2/2005 | Waddell et al. | 514/256 |
| 7,504,402 B2 * | 3/2009 | Waddell et al. | 514/256 |

OTHER PUBLICATIONS

Coats, et al., Thermogravimetric Analysis, The Analyst, vol. 88, pp. 906-924, especially p. 906.*
http://www.chemistrydaily.com/chemistry/Anhydrate. printed Mar. 4, 2013.*
Caira M.R.: "Crystalline Polymorphism of Organic Compounds", Topics in current chemistry, Springer Berlin, DE; vol. 198, Jan. 1, 1998, pp. 163-208, XP001156954; (the whole document).
EPO Search Report for Patent Application PCT/US2009/066939; Completed on Feb. 26, 2010; by Authorized Officer Matés Valdivielso, J.

* cited by examiner

*Primary Examiner* — Susannah Chung
(74) *Attorney, Agent, or Firm* — Richard S. Parr; Catherine D. Fitch

(57) ABSTRACT

Novel crystalline salts of 3-[4-(3-ethanesulfonyl-propyl)-bicyclo[2.2.2]oct-1-yl]-4-methyl-5-(2-trifluoromethyl-phenyl)-4H-1,2,4-triazole are potent inhibitors of 11β-hydroxysteroid dehydrogenase Type 1 and are useful for the treatment of conditions associated with Metabolic Syndrome as well as cognitive impairment. The invention also relates to pharmaceutical compositions containing these novel salts, processes to prepare these salts and their pharmaceutical compositions as well as uses thereof for the treatment of Type 2 diabetes, hyperglycemia, obesity, dyslipidemia, hypertension, and cognitive impairment.

21 Claims, 13 Drawing Sheets

CRYSTALLINE FORMS OF AN INHIBITOR OF 11-β-HYDROXYSTEROID DEHYDROGENASE TYPE 1

FIELD OF THE INVENTION

The present invention relates to novel crystalline forms of an inhibitor of 11β-hydroxysteroid dehydrogenase Type 1. More particularly, the invention relates to novel crystalline anhydrates of 3-[4-(3-ethanesulfonyl-propyl)-bicyclo[2.2.2]oct-1-yl]-4-methyl-5-(2-trifluoromethyl-phenyl)-4H-1,2,4-triazole, which is a potent inhibitor of the 11β-hydroxysteroid dehydrogenase Type 1 (11β-HSD-1) enzyme. These novel crystalline forms of the 11β-HSD-1 inhibitor are useful for the preparation of pharmaceutical compositions containing the inhibitor for the treatment and prevention of diseases and conditions for which an inhibitor of 11β-HSD-1 is indicated, in particular Type 2 diabetes, hyperglycemia, obesity, dyslipidemia, hypertension, and cognitive impairment. The invention further concerns pharmaceutical compositions comprising the novel crystalline polymorphic forms of the present invention; processes for preparing the particular anhydrate forms and their pharmaceutical compositions; and methods of treating conditions for which an inhibitor of 11β-HSD-1 is indicated comprising administering a composition of the present invention.

BACKGROUND OF THE INVENTION

Inhibition of 11β-hydroxysteroid dehydrogenase Type 1 (11β-HSD-1), an enzyme that catalyzes regeneration of active 11-hydroxy glucocorticoids from inactive 11-keto metabolites within target tissues, represents a novel approach to the treatment of the conditions associated with the Metabolic Syndrome, including hypertension, obesity, dyslipidemia, and Type 2 diabetes, also known as non-insulin dependent diabetes mellitus (NIDDM). Inhibitors of this enzyme may also have utility to treat or prevent age-associated cognitive impairment. The therapeutic potential of inhibitors of 11β-HSD-1 has been reviewed: B. R. Walker and J. R. Seckl, "11β-Hydroxysteroid dehydrogenase Type 1 as a novel therapeutic target in metabolic and neurodegenerative disease," *Expert Opin. Ther. Targets*, 7: 771-783 (2003).

U.S. Pat. No. 6,849,636 describes a class of substituted 1,2,4-triazoles, which are potent inhibitors of the 11β-HSD-1 enzyme and therefore useful for the treatment of Type 2 diabetes, hyperglycemia, obesity, dyslipidemia, hypertension, and cognitive impairment. Specifically disclosed in U.S. Pat. No. 6,849,636 is 3-[4-(3-ethanesulfonyl-propyl)-bicyclo[2.2.2]oct-1-yl]-4-methyl-5-(2-trifluoromethyl-phenyl)-4H-1,2,4-triazole.

However, there is no disclosure in U.S. Pat. No. 6,849,636 of the newly discovered crystalline anhydrate forms of 3-[4-(3-ethanesulfonyl-propyl)-bicyclo[2.2.2]oct-1-yl]-4-methyl-5-(2-trifluoromethyl-phenyl)-4H-1,2,4-triazole of structural formula I below (hereinafter referred to as Compound I).

The present invention also discloses novel crystalline methanol and ethanol solvates of Compound I.

SUMMARY OF THE INVENTION

The present invention is concerned with novel crystalline anhydrates of the 11β-hydroxysteroid dehydrogenase Type 1 (11β-HSD-1) inhibitor 3-[4-(3-ethanesulfonyl-propyl)-bicyclo[2.2.2]oct-1-yl]-4-methyl-5-(2-trifluoromethyl-phenyl)-4H-1,2,4-triazole of structural formula I (Compound I). The crystalline anhydrate forms of the present invention have advantages over the previously disclosed amorphous form of 3-[4-(3-ethanesulfonyl-propyl)-bicyclo[2.2.2]oct-1-yl]-4-methyl-5-(2-trifluoromethyl-phenyl)-4H-1,2,4-triazole in the preparation of pharmaceutical compositions, such as ease of processing, handling, and dosing. In particular, they exhibit improved physicochemical properties, such as stability to stress, rendering them particularly suitable for the manufacture of various pharmaceutical dosage forms. The invention also concerns pharmaceutical compositions containing the novel crystalline polymorphs; processes for the preparation of these polymorphic forms and their pharmaceutical compositions; and methods for using them for the prevention or treatment of Type 2 diabetes, hyperglycemia, obesity, dyslipidemia, hypertension, and cognitive impairment.

DETAILED DESCRIPTION OF THE INVENTION

Figure 1:
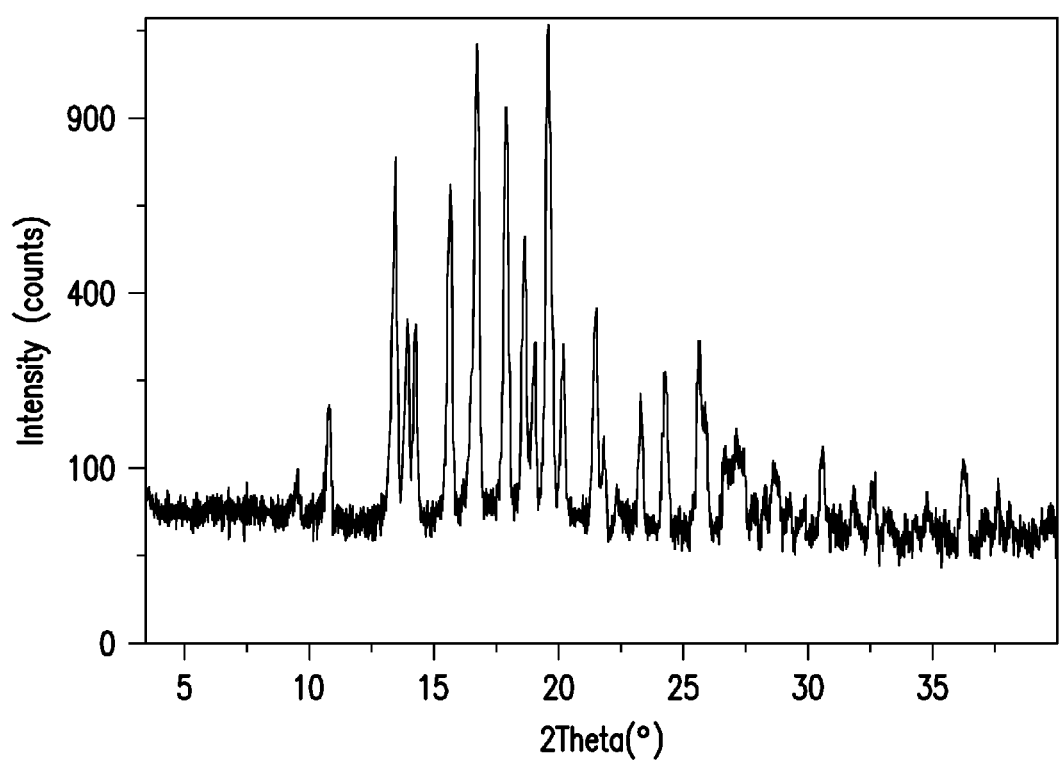
FIG. 1 is a characteristic X-ray diffraction pattern of a crystalline anhydrate, designated Form I, of Compound I of the present invention.

This invention provides novel crystalline anhydrate polymorphic forms of 3-[4-(3-ethanesulfonyl-propyl)-bicyclo[2.2.2]oct-1-yl]-4-methyl-5-(2-trifluoromethyl-phenyl)-4H-1,2,4-triazole of structural formula I (Compound I):

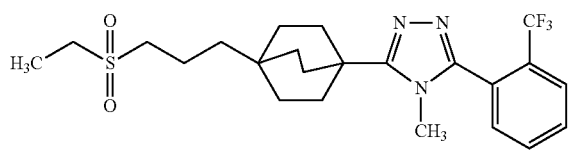 [SMILES: CCS(=O)(=O)CCCC12CCC(c3nnc(-c4ccccc4C(F)(F)F)n3C)(CC1)CC2]

A further embodiment of the present invention provides the Compound I drug substance that comprises a crystalline anhydrate form in a detectable amount. By "drug substance" is meant the active pharmaceutical ingredient (API). The amount of crystalline anhydrate form in the drug substance can be quantified by the use of physical methods such as X-ray powder diffraction (XRPD), solid-state fluorine-19 magic-angle spinning (MAS) nuclear magnetic resonance spectroscopy, solid-state carbon-13 cross-polarization magic-angle spinning (CPMAS) nuclear magnetic resonance spectroscopy, solid state Fourier-transform infrared spectroscopy, and Raman spectroscopy. In a class of this embodiment, about 5% to about 100% by weight of the crystalline anhydrate form is present in the drug substance. In a second class of this embodiment, about 10% to about 100% by weight of the crystalline anhydrate form is present in the drug substance. In a third class of this embodiment, about 25% to about 100% by weight of the crystalline anhydrate form is present in the drug substance. In a fourth class of this embodiment, about 50% to about 100% by weight of the crystalline anhydrate form is present in the drug substance. In a fifth class of this embodiment, about 75% to about 100% by weight of the crystalline anhydrate form is present in the drug substance. In a sixth class of this embodiment, substantially all of the Compound I drug substance is the crystalline anhydrate form, i.e., the Compound I drug substance is substantially phase pure crystalline anhydrate form.

Another aspect of the present invention provides a novel crystalline methanol solvate of Compound I.

Yet another aspect of the present invention provides a novel crystalline ethanol solvate of Compound I.

These crystalline solvates have utility as intermediates in the preparation of the crystalline anhydrates of the present invention.

The present invention further provides a method for the prevention or treatment of clinical conditions for which an inhibitor of 11β-HSD-1 is indicated, which method comprises administering to a patient in need of such prevention or treatment a prophylactically or therapeutically effective amount of a crystalline anhydrate of Compound I or a pharmaceutical composition containing a prophylactically or therapeutically effective amount of a crystalline anhydrate form of Compound I. Such clinical conditions include Type 2 diabetes, hyperglycemia, obesity, dyslipidemia, hypertension, and cognitive impairment.

The present invention also provides for the use of a crystalline anhydrate form of the present invention in the manufacture of a medicament for the prevention or treatment in a mammal of clinical conditions for which an inhibitor of 11β-HSD-1 is indicated.

Another aspect of the present invention provides a crystalline anhydrate form for use in the prevention or treatment in a mammal of clinical conditions for which an inhibitor of 11β-HSD-1 is indicated.

The present invention also provides pharmaceutical compositions comprising a crystalline anhydrate form, in association with one or more pharmaceutically acceptable carriers or excipients. In one embodiment the pharmaceutical composition comprises a prophylactically or therapeutically effective amount of the active pharmaceutical ingredient (API) in admixture with pharmaceutically acceptable excipients wherein the API comprises a detectable amount of a crystalline anhydrate form of the present invention. In a second embodiment the pharmaceutical composition comprises a prophylactically or therapeutically effective amount of the API in admixture with pharmaceutically acceptable excipients wherein the API comprises about 5% to about 100% by weight of a crystalline anhydrate form of the present invention. In a class of this second embodiment, the API in such compositions comprises about 10% to about 100% by weight of such a crystalline anhydrate form. In a second class of this embodiment, the API in such compositions comprises about 25% to about 100% by weight of such a crystalline anhydrate form. In a third class of this embodiment, the API in such compositions comprises about 50% to about 100% by weight of such a crystalline anhydrate form. In a fourth class of this embodiment, the API in such compositions comprises about 75% to about 100% by weight of such a crystalline anhydrate form. In a fifth class of this embodiment, substantially all of the API is in a crystalline anhydrate form of Compound I, i.e., the API is substantially phase pure Compound crystalline anhydrate form.

The compositions in accordance with the invention are suitably in unit dosage forms such as tablets, pills, capsules, powders, granules, sterile solutions or suspensions, metered aerosol or liquid sprays, drops, ampoules, auto-injector devices or suppositories. The compositions are intended for oral, parenteral, intranasal, sublingual, or rectal administration, or for administration by inhalation or insufflation. Formulation of the compositions according to the invention can conveniently be effected by methods known from the art, for example, as described in *Remington's Pharmaceutical Sciences*, 17$^{th}$ ed., 1995.

The dosage regimen is selected in accordance with a variety of factors including type, species, age, weight, sex and medical condition of the patient; the severity of the condition to be treated; the route of administration; and the renal and hepatic function of the patient. An ordinarily skilled physician, veterinarian, or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, 200, and 500 milligrams of the API for the symptomatic adjustment of the dosage to the patient to be treated. A medicament typically contains from about 0.5 mg to about 500 mg of the API, preferably, from about 1 mg to about 200 mg of API. Intravenously, the most preferred doses will range from about 0.1 to about 10 mg/kg/minute during a constant rate infusion. Advantageously, the crystalline anhydrate and monohydrate forms of the present invention may be administered in a single daily dose, or the total daily dosage may be administered in divided doses of two, three or four times daily. Furthermore, the crystalline anhydrate forms of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the Compound I crystalline anhydrate forms described herein can form the API, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active pharmaceutical ingredient can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral API can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The following non-limiting Examples are intended to illustrate the present invention and should not be construed as being limitations on the scope or spirit of the instant invention.

General Conditions for Preferentially Crystallizing Anhydrate Form

The anhydrate form can be crystallized from numerous organic solvents and solvent mixtures. These include methyl acetate, ethyl acetate, isopropyl acetate, n-butyl acetate, isobutyl acetate, toluene, acetone, 2-butanone, tetrahydrofuran, methyl t-butyl ether, and mixtures with pentane, hexanes, heptane, octane, and isooctane. Crystallization can be induced by cooling, evaporation, or addition of a non-polar solvent, such as hexanes or heptane.

General Conditions for Preparing the Crystalline Methanol Solvate

The crystalline methanol solvate can be prepared by stirring a mixture of the anhydrate in methanol for a time sufficient for phase equilibration. The methanol solvate was characterized by physical methods as described below. The methanol solvate can be re-converted into the crystalline anhydrate by drying under vacuum at 40° C. for 3 days.

General Conditions for Preparing the Crystalline Ethanol Solvate

The crystalline ethanol solvate can be prepared by stirring a mixture of the anhydrate in ethanol for a time sufficient for phase equilibration. The ethanol solvate was characterized by physical methods as described below. The ethanol solvate can be re-converted into the crystalline anhydrate by drying under vacuum at 40° C. for 3 days.

SYNTHESIS

Compound I may be prepared using the reactions and techniques described in U.S. Pat. No. 6,849,636.

The following examples further illustrate the crystalline anhydrate forms of Compound I, viz., those polymorphic forms referred to as Form I, Form II and Form III.

Example 1

3-[4-(3-ethanesulfonyl-propyl)-bicyclo[2.2.2]oct-1-yl]-4-methyl-5-(2-trifluoromethyl-phenyl)-4H-1,2,4-triazole crystalline anhydrate (Form II)

Compound I (3-[4-(3-ethanesulfonyl-propyl)-bicyclo[2.2.2]oct-1-yl]-4-methyl-5-(2-trifluoromethyl-phenyl)-4H-1,2,4-triazole) was freebased in two equal portions via treatment of an isopropylacetamide (iPAc) slurry of Compound I with excess aqueous NaOH. Following a filtration step, the two solution portions were then combined and crystallized from iPAc as the Form II crystalline anhydrate.

Example 2

3-[4-(3-ethanesulfonyl-propyl)-bicyclo[2.2.2]oct-1-yl]-4-methyl-5-(2-trifluoromethyl-phenyl)-4H-1,2,4-triazole crystalline anhydrate (Form I)

The Form II crystalline anhydrate was converted to the Form I anhydrate by adjusting the solvent composition to 10% methanol in iPAc, dissolving the material below reflux and seeding at 50° C. After aging overnight at 40° C., the slurry was evaluated and found to be Form I anhydrate exclusively.

Example 3

3-[4-(3-ethanesulfonyl-propyl)-bicyclo[2.2.2]oct-1-yl]-4-methyl-5-(2-trifluoromethyl-phenyl)-4H-1,2,4-triazole crystalline anhydrate (Form III)

It was discovered that if the aging step described above (overnight at 40° C.) is skipped, and the material is allowed to cool to room temperature, the resultant mixture is found to be Forms I and III of the crystalline anhydrate. Using the Form III (as little as 0.5 weight %) to seed a room temperature iPAc slurry (or a 10% methanol/iPAc slurry) of Form I anhydrate results in complete turnover, following a 14-16 hour aging period to the more thermodynamically stable Form III.

Form III can also be directly crystallized from the free base in an iPAc or methanol/iPAc solution upon seeding at 30-35° C. (or at room temperature) with Form III material.

X-ray powder diffraction studies are widely used to characterize molecular structures, crystallinity, and polymorphism. The X-ray powder diffraction patterns of the crystalline polymorphs of the present invention were generated on a Philips Analytical X'Pert PRO X-ray Diffraction System with PW3040/60 console. A PW3373/00 ceramic Cu LEF X-ray tube K-Alpha radiation was used as the source.

FIG. 1 shows a characteristic X-ray diffraction pattern for the crystalline anhydrate form (Form I) of Compound I of the present invention. The anhydrate form exhibited characteristic reflections corresponding to d-spacings of 6.56, 6.33, 6.19, 5.63, 5.27, 4.93, 4.74, 4.65, 4.51, and 4.37 angstroms.

Figure 4:
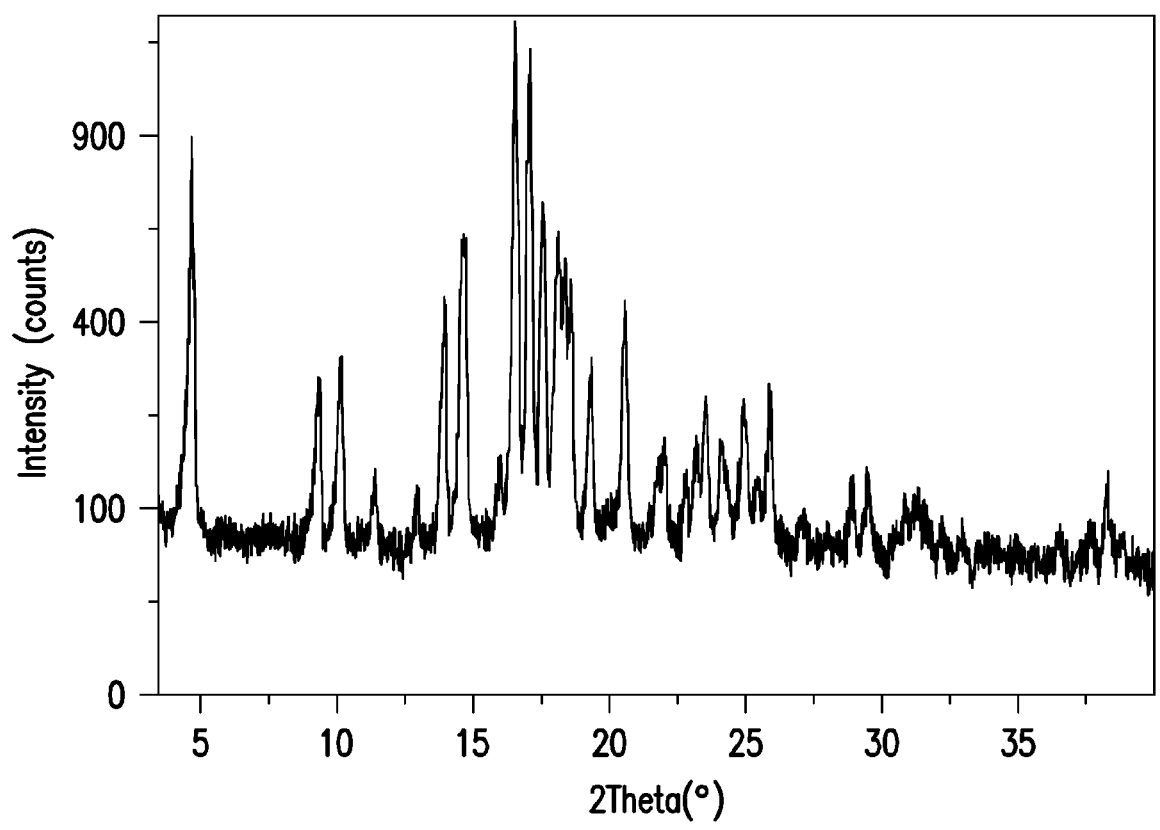
FIG. 4 is a characteristic X-ray diffraction pattern of a crystalline anhydrate, designated Form II, of Compound I of the present invention.

FIG. 4 shows an X-ray diffraction pattern for the crystalline anhydrate form (Form II) of Compound I of the present invention. This anhydrate form exhibited characteristic reflections corresponding to d-spacings of 18.33, 9.37, 8.62, 6.28, 6.02, 5.97, 5.30, 5.14, 5.01, and 4.86 angstroms.

Figure 6:
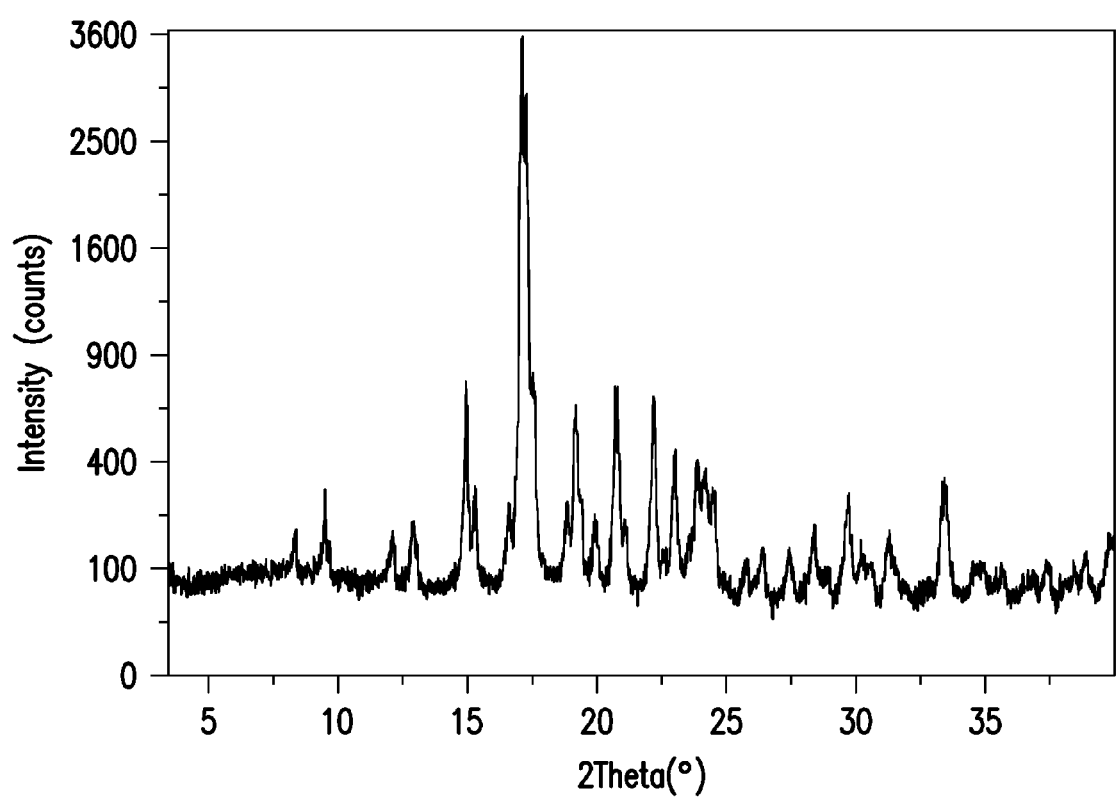
FIG. 6 is a characteristic X-ray diffraction pattern of a crystalline anhydrate, designated Form III, of Compound I of the present invention.

FIG. 6 shows an X-ray diffraction pattern for the crystalline anhydrate (Form III) of the present invention. This anhydrate exhibited characteristic reflections corresponding to d-spacings of 9.26, 5.90, 5.78, 5.33, 5.16, 5.10, 5.03, 4.69, 4.61, and 4.26 angstroms.

Figure 9:
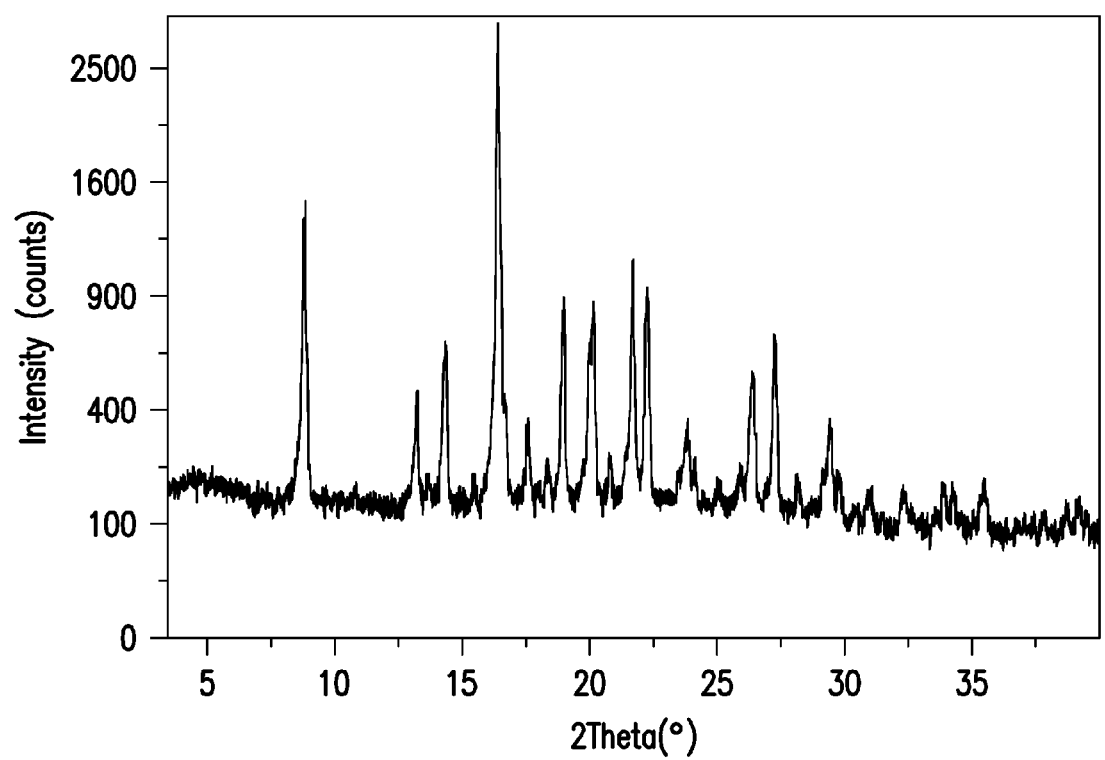
FIG. 9 is a characteristic X-ray diffraction pattern of the crystalline methanol solvate of Compound I of the present invention.

FIG. 9 shows a characteristic X-ray diffraction pattern for the crystalline methanol solvate of Compound I of the present invention. The methanol solvate exhibited characteristic reflections corresponding to d-spacings of 9.88, 6.13, 5.36, 4.65, 4.43, 4.39, 4.08, 3.98, 3.36 and 3.26 angstroms.

Figure 11:
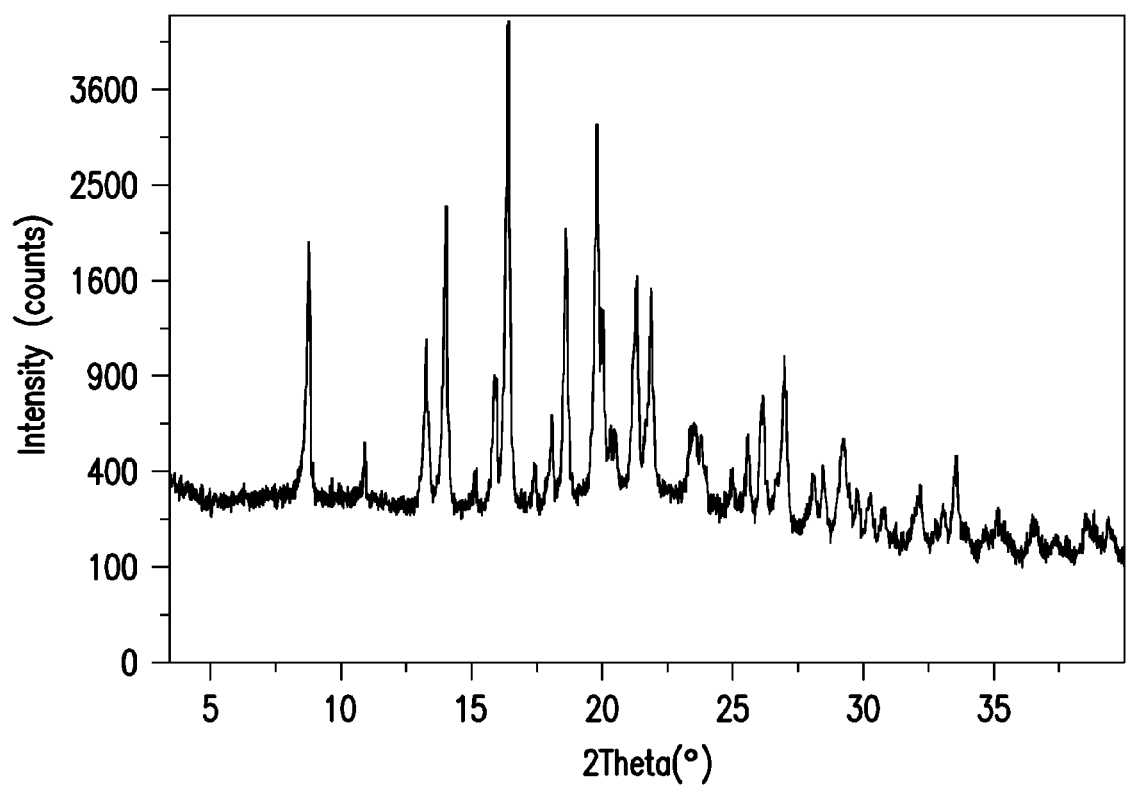
FIG. 11 is a characteristic X-ray diffraction pattern of the crystalline ethanol solvate of Compound I of the present invention.

FIG. 11 is a characteristic X-ray diffraction pattern for the crystalline ethanol solvate of Compound I of the present invention. The ethanol solvate exhibited characteristic reflections corresponding to d-spacings 10.03, 6.66, 6.29, 5.38, 4.74, 4.46, 4.41, 4.15, 4.04 and 3.30 angstroms.

In addition to the X-ray powder diffraction patterns described above, the crystalline polymorphic forms of Compound I of the present invention were further characterized by their solid-state carbon-13 nuclear magnetic resonance (NMR) spectra. The solid-state carbon-13 NMR spectrum was obtained on a Bruker DSX 400WB NMR system using a Bruker 4 mm double resonance CPMAS probe. The carbon-13 NMR spectrum utilized proton/carbon-13 cross-polarization magic-angle spinning with variable-amplitude cross polarization. The sample was spun at 15.0 kHz, and a total of 1024 scans were collected with a recycle delay of 5 seconds. A line broadening of 40 Hz was applied to the spectrum before FT was performed. Chemical shifts are reported on the TMS scale using the carbonyl carbon of glycine (176.03 p.p.m.) as a secondary reference.

Figure 2:
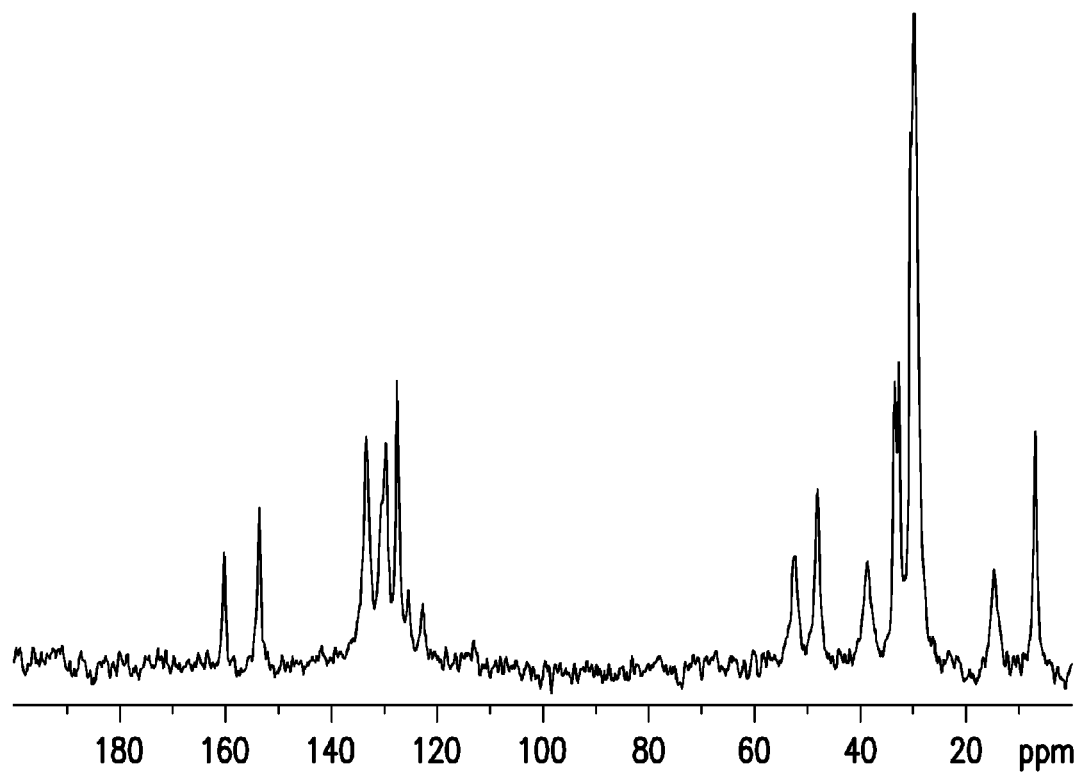
FIG. 2 is a carbon-13 cross-polarization magic-angle spinning (CPMAS) nuclear magnetic resonance (NMR) spectrum of a crystalline anhydrate, designated Form I, of Compound I of the present invention.

FIG. 2 shows the solid state carbon-13 CPMAS NMR spectrum for the crystalline anhydrate form (Form I) of Compound I. This crystalline anhydrate form exhibited characteristic signals with chemical shift values of 160.2, 153.6, 133.4, 129.8, 127.6, 48.0, 33.4, 32.7, 29.6, and 6.9 p.p.m.

Figure 5:
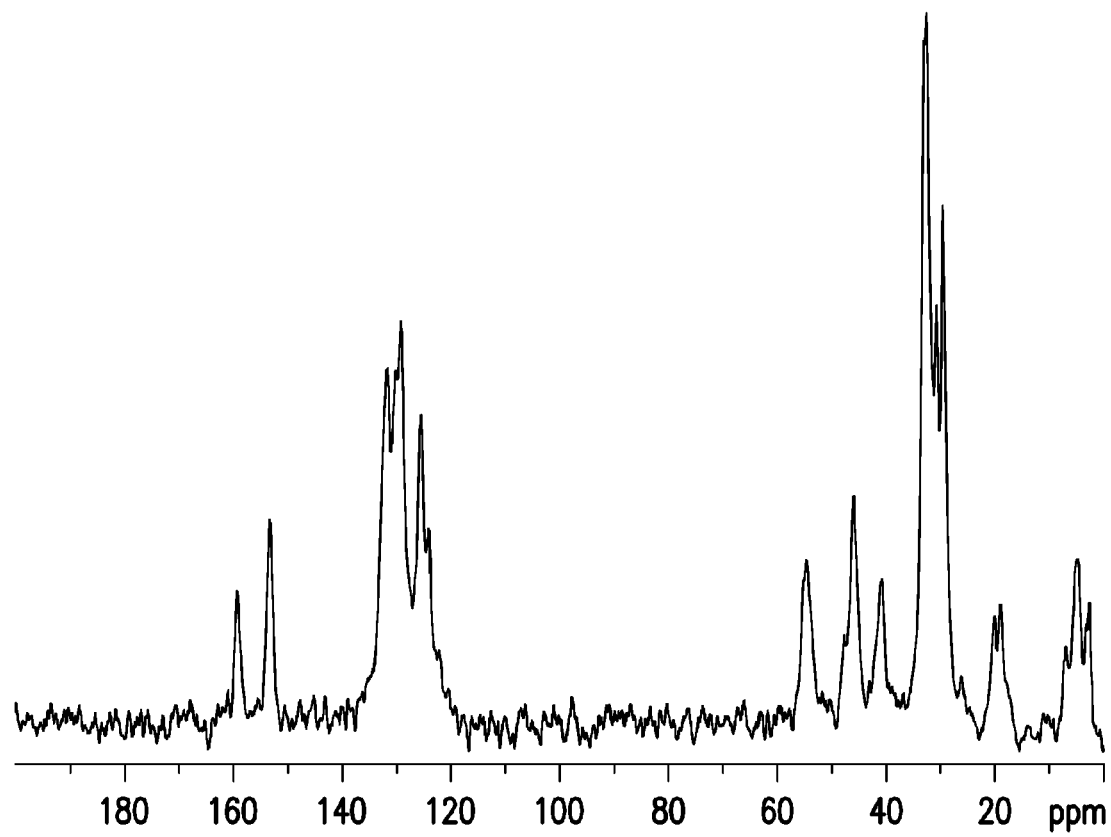
FIG. 5 is a carbon-13 cross-polarization magic-angle spinning (CPMAS) nuclear magnetic resonance (NMR) spectrum of a crystalline anhydrate, designated Form II, of Compound I of the present invention.

FIG. 5 shows the solid state carbon-13 CPMAS NMR spectrum for the crystalline anhydrate form (Form II) of Compound I. This crystalline anhydrate form exhibited characteristic signals with chemical shift values of 153.2, 131.6, 129.0, 125.4, 54.4, 45.8, 32.3, 30.6, 29.4, and 4.8 p.p.m.

Figure 7:
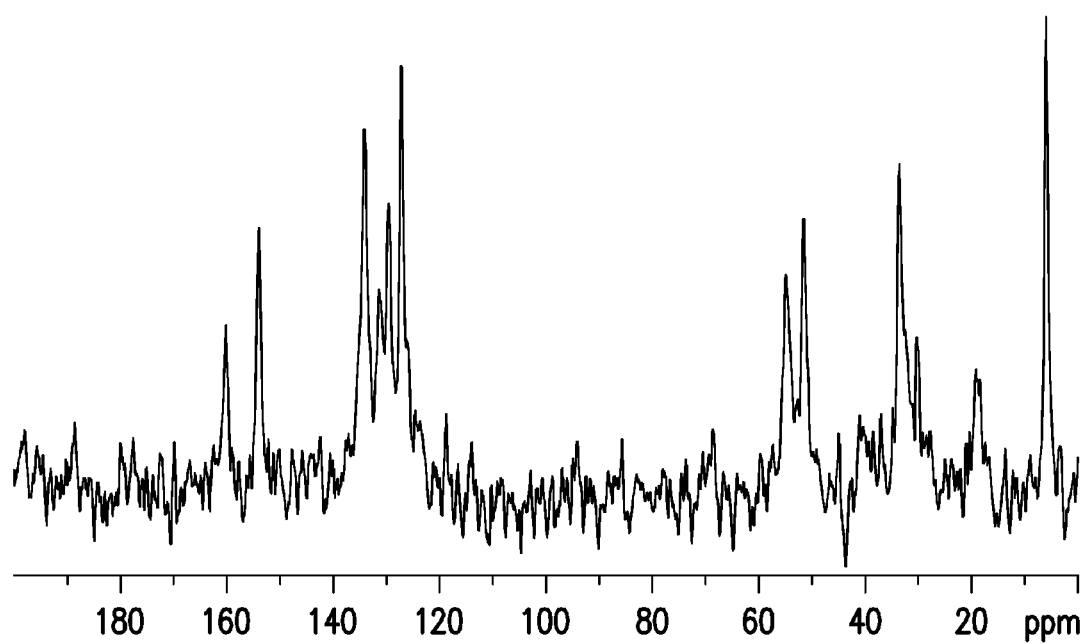
FIG. 7 is a carbon-13 cross-polarization magic-angle spinning (CPMAS) nuclear magnetic resonance (NMR) spectrum of a crystalline anhydrate, designated Form III, of Compound I of the present invention.

FIG. 7 shows the solid state carbon-13 CPMAS NMR spectrum for the crystalline anhydrate form (Form III) of Compound I. This crystalline anhydrate form exhibited characteristic signals with chemical shift values of 153.2, 153.9, 134.0, 131.4, 129.5, 127.0, 54.8, 51.5, 33.4, and 5.9 p.p.m.

Additionally, differential scanning calorimetry (DSC) was performed. DSC data were acquired using TA Instruments DSC 2910 (or equivalent instrumentation). Between 2 and 6 mg sample was weighed into an open pan. This pan was then crimped and placed at the sample position in the calorimeter cell. An empty pan was placed at the reference position. The calorimeter cell was closed and a flow of nitrogen was passed through the cell. The heating program was set to heat the sample at a heating rate of 10° C./min to a temperature of approximately 250° C. The heating program was started. When the run was completed, the data were analyzed using the DSC analysis program contained in the system software. The melting endotherm was integrated between baseline temperature points that are above and below the temperature range over which the endotherm was observed. The data reported are the onset temperature, peak temperature and enthalpy.

Figure 3:
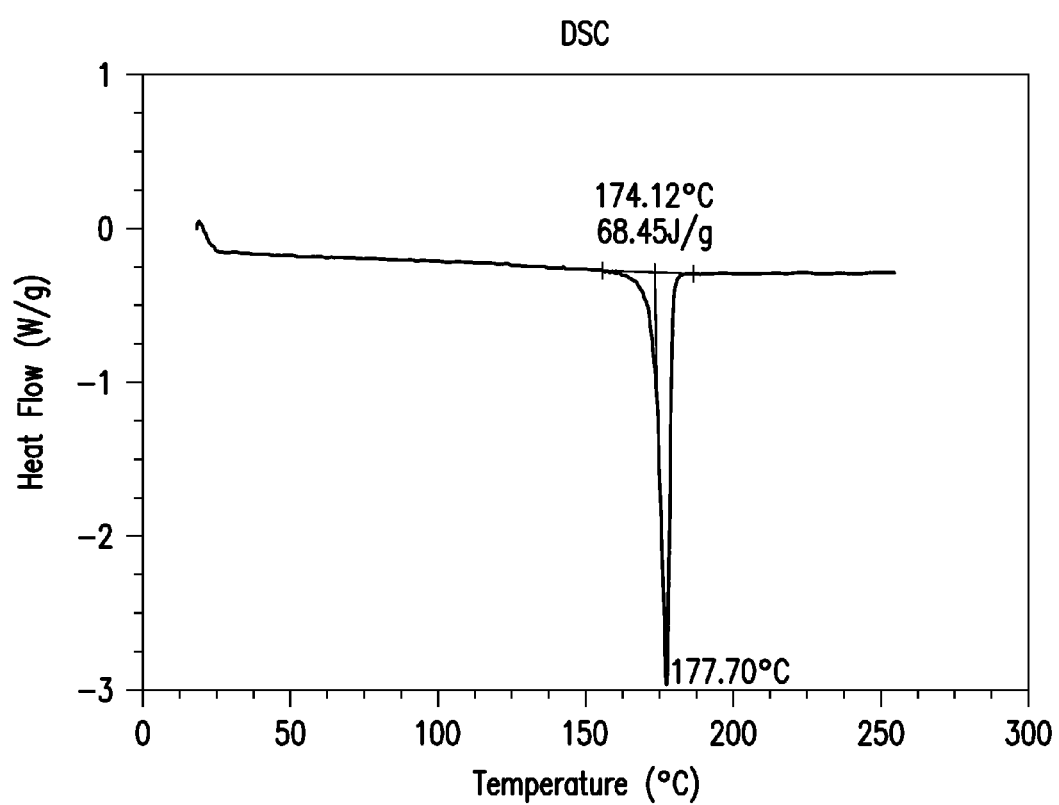
FIG. 3 is a typical differential scanning calorimetry (DSC) curve of a crystalline anhydrate, designated Form I, of Compound I of the present invention.

FIG. 3 shows the differential calorimetry scan for the crystalline anhydrate form (Form I) of Compound I. This crystalline anhydrate form exhibited a melting endotherm with an onset temperature of 174.1° C., a peak temperature of 177.7° C., and an enthalpy of 68.5 J/g.

Figure 8:
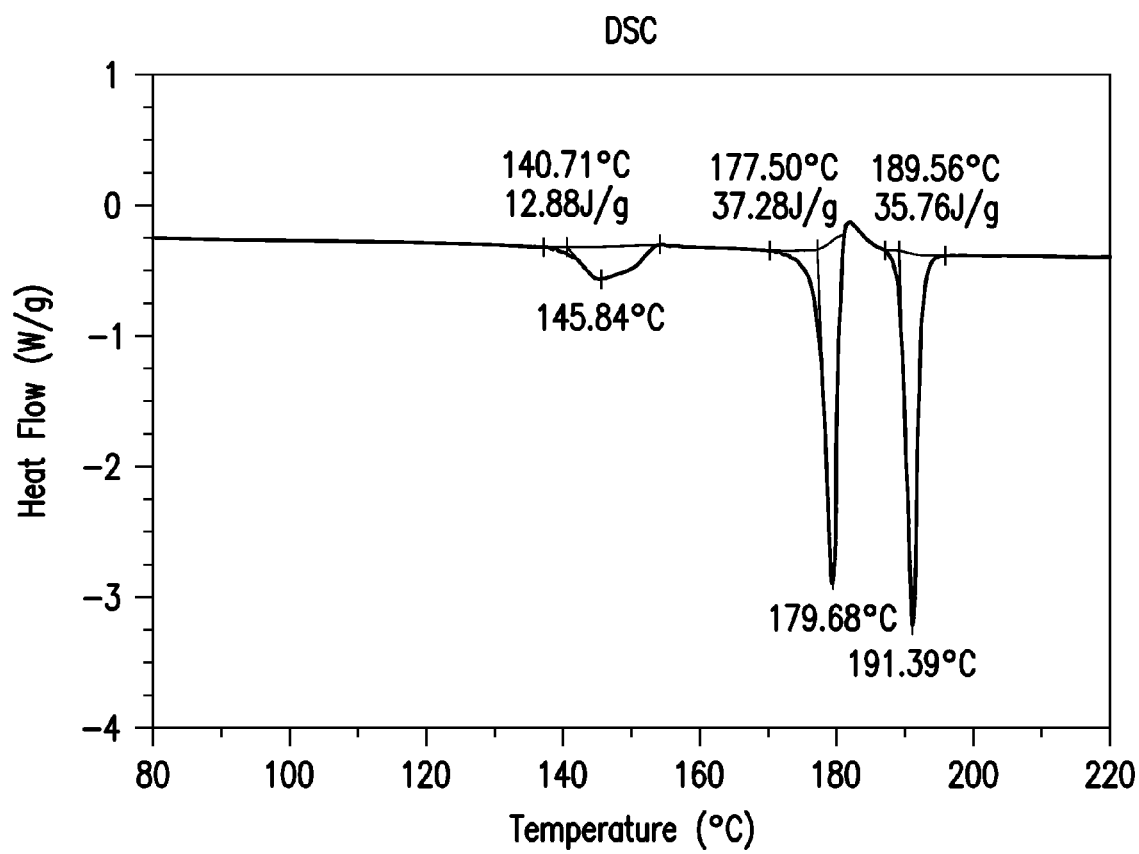
FIG. 8 is a typical differential scanning calorimetry (DSC) curve of a crystalline anhydrate, designated Form III, of Compound I of the present invention.

FIG. 8 shows the differential calorimetry scan for the crystalline anhydrate form (Form III) of Compound I. This crystalline anhydrate form exhibited a first endotherm with an onset temperature of 177.5° C., a peak temperature of 179.7° C., and an enthalpy of 37.3 J/g. The first thermal event was followed by a second endotherm, with an onset temperature of 189.6° C. and a peak temperature of 191.4° C. and an enthalpy of 35.8 J/g.

A Perkin Elmer model TGA 7 (or equivalent instrument) was used to obtain the thermogravimetric analysis (TGA) curves. Experiments were performed under a flow of nitrogen and using a heating rate of 10° C./min to a maximum temperature of approximately 250° C. After automatically taring the balance, 5 to 20 mg of sample was added to the platinum pan, the furnace was raised, and the heating program started. Weight/temperature data were collected automatically by the instrument. Analysis of the results was carried, out by selecting the Delta Y function within the instrument software and choosing the temperatures between which the weight loss was to be calculated. Weight losses are reported up to the onset of decomposition/evaporation.

Figure 10:
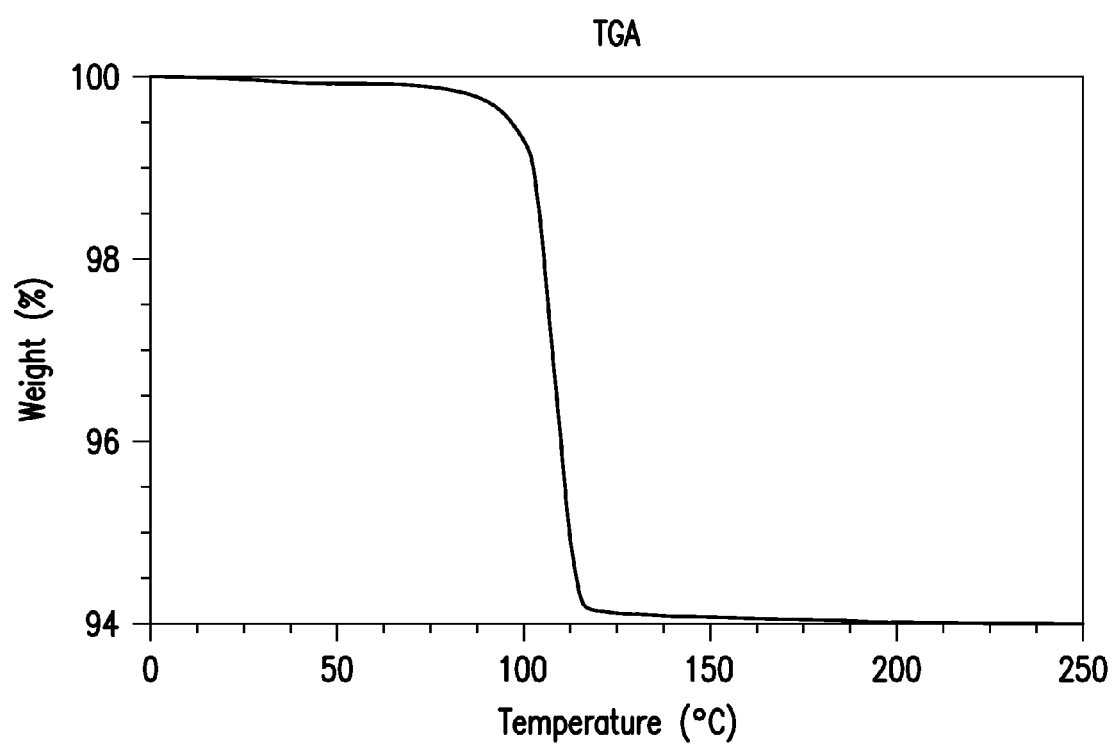
FIG. 10 is a typical thermogravimetric analysis (TGA) curve of the crystalline methanol solvate of Compound I of the present invention.

FIG. 10 shows a characteristic thermogravimetric analysis (TGA) curve for the crystalline methanol solvate form of Compound I. TGA indicated a weight loss of about 5.8% at 120° C.

Figure 13:
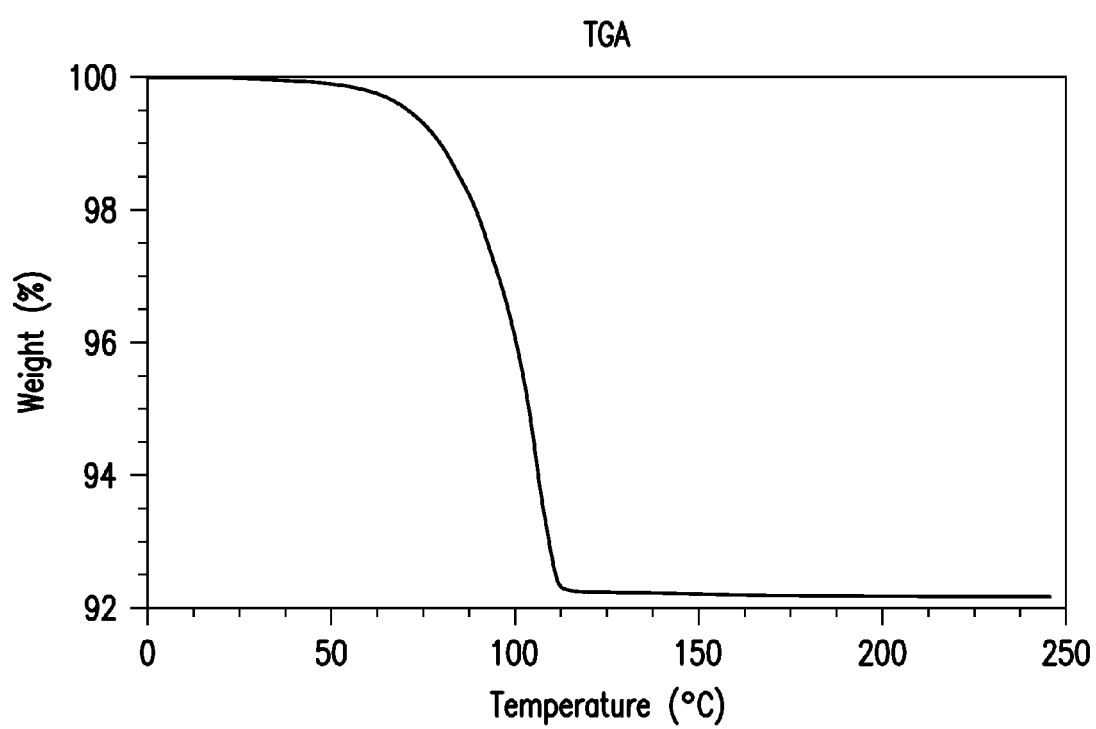
FIG. 13 is a typical thermogravimetric analysis (TGA) curve of the crystalline ethanol solvate of Compound I of the present invention.

FIG. 13 shows a characteristic thermogravimetric analysis (TGA) curve for the crystalline ethanol solvate of Compound I. TGA indicated a weight loss of about 7.8% at 120° C.

Example of a Pharmaceutical Composition:

A crystalline anhydrate form of the present invention was formulated into a capsule formulation as follows. A 100 mg potency capsule was composed of 100 mg of the API, 190 mg of microcrystalline cellulose, and about 95 mg gelatin as in #0 white opaque gelatin capsule. The API and microcrystalline cellulose were first blended, and the mixture was then encapsulated in gelatin capsules.

What is claimed is:

1. A crystalline anhydrate of 3-[4-(3-ethanesulfonyl-propyl)-bicyclo[2.2.2]oct-1-yl]-4-methyl-5-(2-trifluoromethylphenyl)-4H-1,2,4-triazole of structural formula I:

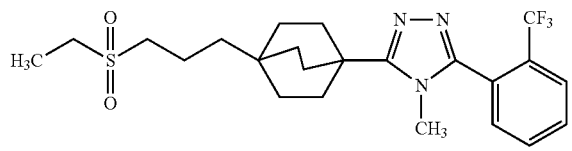 [SMILES: CCS(=O)(=O)CCCC12CCC(c3nnc(-c4ccccc4C(F)(F)F)n3C)(CC1)CC2]

characterized by characteristic reflections obtained from the X-ray powder diffraction pattern at spectral d-spacings of about 6.56, 6.33, 6.19, 5.63, 5.27, 4.93, 4.74, 4.65, 4.51 and 4.37 angstroms.

2. The crystalline anhydrate of claim 1 further characterized by the X-ray powder diffraction pattern of FIG. 1.

3. A crystalline anhydrate of claim 1 characterized by a solid-state carbon-13 CPMAS nuclear magnetic resonance spectrum showing signals with chemical shift values of about 160.2, 153.6, 133.4, 129.8, 127.6, 48.0, 33.4, 32.7, 29.6, and 6.9 p.p.m.

4. The crystalline anhydrate of claim 3 characterized by the solid state carbon-13 CPMAS nuclear magnetic resonance spectrum of FIG. 2.

5. A crystalline anhydrate of claim 1 characterized by the differential scanning calorimetric (DSC) curve of FIG. 3.

6. A crystalline anhydrate of 3-[4-(3-ethanesulfonyl-propyl)-bicyclo[2.2.2]oct-1-yl]-4-methyl-5-(2-trifluoromethylphenyl)-4H-1,2,4-triazole of structural formula I:

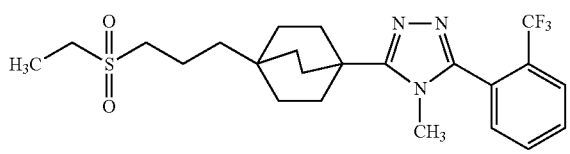 [SMILES: CCS(=O)(=O)CCCC12CCC(c3nnc(-c4ccccc4C(F)(F)F)n3C)(CC1)CC2]

characterized by characteristic reflections obtained from the X-ray powder diffraction pattern at spectral d-spacings of about 18.33, 9.37, 8.62, 6.28, 6.02, 8.08, 6.49, 5.43, 5.39, 4.38, 4.10, 3.18, and 2.74 angstroms.

7. The crystalline anhydrate of claim 6 further characterized by the X-ray powder diffraction pattern of FIG. 4.

8. A crystalline anhydrate of claim 6 characterized by a solid-state carbon-13 CPMAS nuclear magnetic resonance spectrum showing signals with chemical shift values of about 153.2, 131.6, 129.0, 125.4, 54.4, 45.8, 32.3, 30.6, 29.4, and 4.8 p.p.m.

9. The crystalline anhydrate of claim 8 characterized by the solid-state carbon-13 CPMAS nuclear magnetic resonance spectrum of FIG. 5.

10. A crystalline anhydrate of 3-[4-(3-ethanesulfonyl-propyl)-bicyclo[2.2.2]oct-1-yl]-4-methyl-5-(2-trifluoromethyl-phenyl)-4H-1,2,4-triazole of structural formula I:

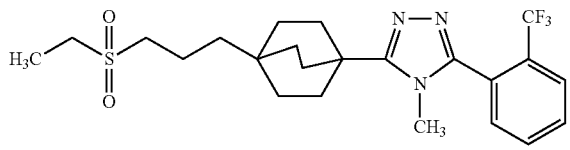 [SMILES: CCS(=O)(=O)CCCC12CCC(c3nnc(-c4ccccc4C(F)(F)F)n3C)(CC1)CC2]

characterized by characteristic reflections obtained from the X-ray powder diffraction pattern at spectral d-spacings of about 9.26, 5.90, 5.78, 5.33, 5.16, 5.10, 5.03, 4.69, 4.61, and 4.26 angstroms.

11. The crystalline anhydrate of claim 10 further characterized by the X-ray powder diffraction pattern of FIG. 6.

12. A crystalline anhydrate of claim 10 characterized by a solid-state carbon-13 CPMAS nuclear magnetic resonance spectrum showing signals with chemical shift values of about 160.1, 153.9, 134.0, 131.4, 129.5, 127.0, 54.8, 51.5, 33.4, and 5.9 p.p.m.

13. The crystalline anhydrate of claim 12 characterized by the solid-state carbon-13 CPMAS nuclear magnetic resonance spectrum of FIG. 7.

14. A crystalline anhydrate of claim 10 characterized by the differential scanning calorimetric (DSC) curve of FIG. 8.

15. The crystalline methanol solvate of 3-[4-(3-ethanesulfonyl-propyl)-bicyclo[2.2.2]oct-1-yl]-4-methyl-5-(2-trifluoromethyl-phenyl)-4H-1,2,4-triazole of structural formula I:

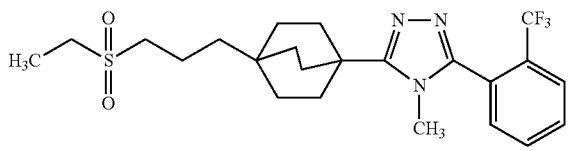 [SMILES: CCS(=O)(=O)CCCC12CCC(c3nnc(-c4ccccc4C(F)(F)F)n3C)(CC1)CC2]

characterized by characteristic reflections obtained from the X-ray powder diffraction pattern at spectral d-spacings of about 9.88, 6.13, 5.36, 4.65, 4.43, 4.39, 4.08, 3.98, 3.36, and 3.26 angstroms.

16. The crystalline methanol solvate of claim 15 further characterized by the X-ray powder diffraction pattern of FIG. 9.

17. The crystalline methanol solvate of claim 15 characterized by the thermogravimetric analysis (TGA) curve of FIG. 10.

18. The crystalline ethanol solvate of 3-[4-(3-ethanesulfonyl-propyl)-bicyclo[2.2.2]oct-1-yl]-4-methyl-5-(2-trifluoromethyl-phenyl)-4H-1,2,4-triazole of structural formula I:

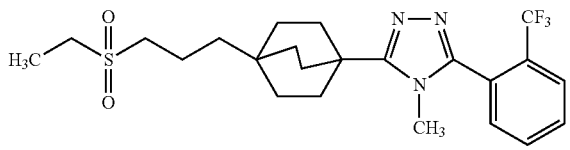 [SMILES: CCS(=O)(=O)CCCC12CCC(c3nnc(-c4ccccc4C(F)(F)F)n3C)(CC1)CC2]

characterized by characteristic reflections obtained from the X-ray powder diffraction pattern at spectral d-spacings of about 10.03, 6.66, 6.29, 5.38, 4.74, 4.46, 4.41, 4.15, 4.04, and 3.30 angstroms.

19. The crystalline ethanol solvate of claim 18 further characterized by the X-ray powder diffraction pattern of FIG. 11.

Figure 12:
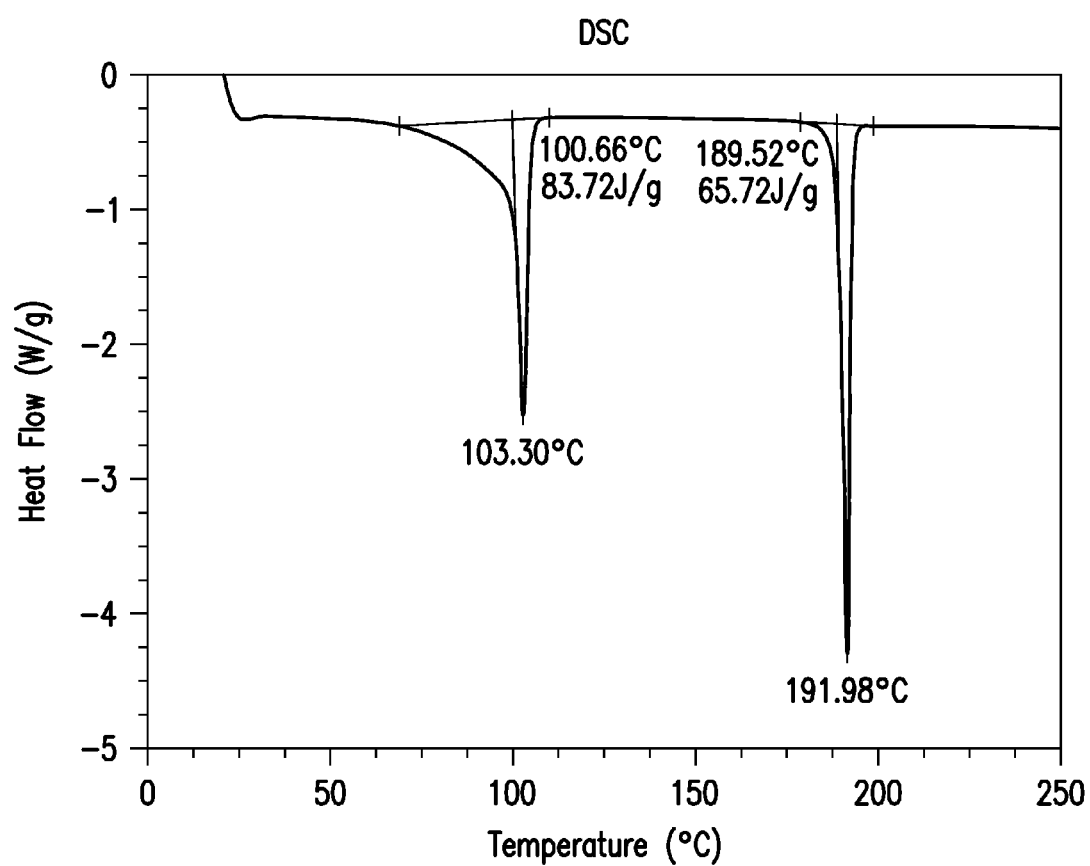
FIG. 12 is a typical differential scanning calorimetry (DSC) curve of the crystalline ethanol solvate of Compound I of the present invention.

20. The crystalline ethanol solvate of claim 18 characterized by the differential scanning calorimetric (DSC) curve of FIG. 12.

21. The crystalline ethanol solvate of claim 18 characterized by the thermogravimetric analysis (TGA) curve of FIG. 13.

\* \* \* \* \*